United States Patent [19]
Morito et al.

[11] Patent Number: 5,952,651
[45] Date of Patent: Sep. 14, 1999

[54] LASER MANIPULATION APPARATUS AND CELL PLATE USED THEREFOR

[75] Inventors: Yuhkoh Morito; Shuji Shikano, both of Yokohama; Chie Nishioka, Atsugi; Koji Horio, Yokohama, all of Japan

[73] Assignees: Moritex Corporation, Tokyo; Japan Science and Technology Corporation, Saitama, both of Japan

[21] Appl. No.: 08/872,177

[22] Filed: Jun. 10, 1997

[30] Foreign Application Priority Data

Jun. 10, 1996 [JP] Japan ..................................... 8-147127
Aug. 26, 1996 [JP] Japan ..................................... 8-223358

[51] Int. Cl.$^6$ ..................................................... H05H 3/04
[52] U.S. Cl. .......................................................... 250/251
[58] Field of Search ............................................. 250/251

[56] References Cited

U.S. PATENT DOCUMENTS

| | | |
|---|---|---|
| 4,893,886 | 1/1990 | Ashkin et al. . |
| 5,100,627 | 3/1992 | Buican et al. . |
| 5,512,745 | 4/1996 | Finer et al. ............................. 250/251 |
| 5,689,109 | 11/1997 | Schutze ................................. 250/251 |

OTHER PUBLICATIONS

Sakano et al., "A study on the damages due to the Lasser Irradiation", Department of Electrical and Electronic Engineering, Toyohashi University of Technology, Oct. 1991, pp. 279–282.

Bryant et al., "Absolute Optical Cross Sections of Cells and Chloroplasts", Archives of Biochemistry and Biophysics 135, 1969, pp. 97–108.

Dinkel et al., "Remote two–photon excited fluorescence sensing in a stimulated fermentation broth", Analytica Chimica Acta, 236/1992, pp.131–136.

Ashkin et al., "Optical Trapping and Manipulation of Viruses and Bacteria", Mar. 20, 1987, pp. 1517–1520.

Ashkin et al., "Optical trapping and manipulation of single cells using infrared laser beams", Dec. 1987, Nature vol. 330, pp.769–771.

*Primary Examiner*—Jack I. Berman
*Attorney, Agent, or Firm*—Pillsbury Madison & Sutro LLP

[57] ABSTRACT

A laser manipulation apparatus for trapping and separating an optional micro-sample comprising a cell plate having a first cell for storing a liquid medium containing micro-sample s and a second cell for storing a liquid medium not containing micro-sample s each of the first and second cells being opened at the upper surface, in communication with each other by way of a narrow induction channel for inhibiting free movement of the micro-sample s, an optical trapping system for irradiating and trapping a single micro-sample out of a group of micro-sample s dispersed and suspended in the liquid medium stored in the first cell and a sample separation device for moving the single micro-sample from the first cell through the induction channel into the second cell.

2 Claims, 11 Drawing Sheets

Absorption Of Escherichia Coli

LASER MANIPULATION APPARATUS AND CELL PLATE USED THEREFOR

BACKGROUND OF THE INVENTION

1. Field of the Invention

The present invention concerns a laser manipulation apparatus for trapping a micro-sample selected from a group of micro-sample s dispersed and suspended in a liquid medium under the view field of a microscope and separating the trapped sample from other micro-sample s.

2. Statement Related Art

For instance, *Escherichia coli* are often used as micro-sample s for genetic manipulation. In this case, the genetic manipulation is applied by dispersing the samples in a predetermined liquid medium, then *Escherichia coli* dispersed in the liquid medium are sucked together with the liquid medium by a micropipette or the like, transferred into and cultured in a culture vessel and a great amount of DNA are reproduced.

However, not all of the *Escherichia coli* dispersed in the liquid medium are genetically manipulated because of the individual difference, and a plurality of *Escherichia coli* are sucked simultaneously into a micropipette, so that cultured *Escherichia coli* comprise mixture of those with and without genetic manipulation and the yield for those applied with the genetic manipulation is low.

If culture from a single *Escherichia coli* is possible, pure culture is enabled and only *Escherichia coli* subjected to genetic manipulation can be obtained at 100% yield if the starting single *Escherichia coli* was genetically manipulated.

When it is intended to take out only one of micro-sample s such as biological particles or micro-particles under the view field of an optical microscope, there is no substantial problem if the size of the samples is somewhat large. However, if it is too small as *Escherichia coli*, since the view field is restricted in view of the optical property of lenses, it is extremely difficult to take out the aimed sample while microscopically confirming that other micro-sample s are not mixed.

For instance, in a case of taking-out a biological particle of 100 μm length, it can be taken-out by using a micropipette of 200 μm diameter while observing that other biological particles are not mixed under a microscope having a lens with a resolution power of 10 μm, a focal depth of 300 μm, NA=0.034 and a view field diameter of 10 mm. On the other hand, in a case of taking-out a biological particle of only about 1 μm length such as *Escherichia coli* sucked together with 1 mm$^3$ of a liquid medium into a micropipette, it can not be confirmed that other biological particles are not mixed even if a lens used has a resolution power of 0.26 μm and NA=1.3 (oil-immersed objective lens having 100 magnification factor), which are the limit of an optical lens, because the focal depth is only 0.2 μm and the view field is only 200 μm.

Further, even if the micro-sample has such a size as can be confirming by a microscope, if a great number of biological particles or like other particles are present in 1 mm$^3$ of a liquid medium to be sucked into a micropipette, the great number of such individuals may possibly be sucked simultaneously or deposited at the top end of the micropipette and mixed upon dropping of the liquid medium. After all, although it is possible to take-out a great number of biological particles simultaneously by sucking a great amount of a liquid medium, it is difficult to take out only one of biological particles or like other particles, and this enforces troublesome repeating diluting operation.

Further, even if the density of micro-sample s present in the liquid medium is low, those moving at a relatively high speed such as *Escherichia coli* (several μm to several tens μm/s) are difficult to be trapped since the operation of a micropipette following after the movement results in stirring of the liquid medium to flow the biological particles by the stream.

It has been proposed, in U.S. Pat. No. 5,100,627, a chamber comprising sample supply channels for flowing a liquid medium in which micro-sample s are dispersed and sample separation channels for flowing a liquid medium in which no micro-sample s are dispersed. They are formed in parallel with each other, and each of the channels is in communication by an interconnection channel. The interconnection channel is conducted intermittently by a bubble valve thereby taking out the micro-sample flowing through the sample supply channel only by one to the sample separation channel.

In this bubble valve, a bubble channel for flowing a bubble-containing liquid medium is formed in parallel with the sample supply channel and the sample separation channel and crossing the interconnection channel, so that the interconnection channel is conducted by filling a liquid medium to the intersection between the bubble channel and the interconnection channel and shut by situating the bubble.

However, in this structure, it is extremely difficult to control the pressure balance between the liquid medium supplied by the bubble channel and the liquid medium filled in the sample supply channel and the sample separation channel.

For instance, when the bubble or the liquid medium is supplied by the bubble channel, since the liquid medium in other channels flows under the effect thereof, it is extremely difficult and not practical to carry out on-off control only for the interconnection channel as desired with no effect on other channels.

Meanwhile, in a case of optically trapping a biological particle, trapping has been conducted by using an IR laser as a light source (refer to Japanese Patent Publication Hei 5-6136, on the basis of the priority of U.S. Pat. No. 4,893, 886).

This is based on the result of experiment by Ashkin, et al that light-induced biological damages were observed when biological particles were trapped by using a visible light laser (Ar laser: wavelength at 514 nm) as a light source, whereas no light-induced biological damages were observed when biological samples are trapped by using an IR laser (YAG laser: wavelength at 1064 nm) as a light source.

However, the optical trap by the IR laser involves the following problems compared with the optical trap by the visible light.

At first, since the visible light can be seen, a danger, if caused by entrance of light to an eye, can be avoided by closing an eye lid or interrupting the light, whereas the IR light can not be seen and is liable to damage eyes with no awareness for the entrance of light.

Secondly, since the visible light can be recognized visually, adjustment for the optical system is easy when the apparatus is set, whereas the IR light can not be recognized visually and, therefore, adjustment for the optical system is difficult.

Thirdly, a trapping force is generally weak as a wavelength is longer. For instance, for a polyethylene latex particle of 3 μm size, the trapping force of a YAG laser (IR light: wavelength at 1064 nm) is smaller by 25% than the trapping force of a red light (visible light: wavelength at 600 nm). In the case of 1 μm particle size, the trapping force of the YAG laser is smaller by 45% as compared with the trapping force of the red light.

Fourthly, optical trapping is conducted at a focal position of an objective lens (converging optical system), a beam spot diameter at the focal position is in proportion with a wavelength and the beam spot diameter increases as the wavelength is longer, so that it is more difficult to trap a small sample by the IR light as compared with the visible light.

Fifthly, general-purpose parts for usual microscopes such as lenses, mirrors and other optical elements are used for the laser manipulation apparatus in order to reduce the cost. Since they are designed for the light in the visible light region, if a light in the IR region is used, the optical transmittance is decreased to reduce the efficiency of utilizing the laser light, as well as aberration is increased to lower the light convergence.

For example, in a case of an objective lens of 100 magnification factor, optical transmittance is more than 90% for the red light (visible light: wavelength at 600 nm), whereas the optical transmittance for the YAG laser (IR light: wavelength at 1064 nm) is lowered to less than 30%. Accordingly, in a case of using the IR light, a light source having a power about three times as large as that of the visible light has to be used if it is intended to irradiate a light at a same level of intensity.

Further, in a case of using the IR light, since the aberration of the lens is large, the beam spot diameter at the focal position increases to reduce the trapping force for a small sample.

The foregoings are concerned with the matters of lens design. Accordingly, it is of course technically possible to design such that IR transmittance is improved or aberration is reduced. Then, if optical lenses adapted exclusively for the IR light are used, the problems for optical transmittance or aberration can be overcome. However, in a case of design and manufacture of such products for exclusive use, it results in another problem of increasing the manufacturing cost to increase the cost for the entire apparatus.

The IR light has been used for optical trapping of biological particles irrespective of various drawbacks compared with the visible light, because it is highly demanded for separating a single sample alive, for example, in a case of culturing *Escherichia coli* applied with genetic manipulation.

In a case of using the technique of optical trapping for taking out a single *Escherichia coli*, there is a premise that the *Escherichia coli* is taken out alive as it is. An identical conclusion is also derived from the study of Sakano, et al in addition to Ashkin described above (articles of Static Electricity Society/October, 1991).

According to Sakano, et al, it was reported that when an Ar laser (wavelength at 514 nm) was irradiated to *Escherichia coli* at 0.64 mW/$\mu m^2$, movement stopped in about 7 sec, whereas the movement did not stop even if irradiation was conducted by applying a YAG laser (wavelength at 1064 nm) for more than two hours at a double intensity of 1.28 mW/$\mu m^2$.

Then, the light-induced damages were compared between the case of 514 nm and 1064 nm wavelength, and it was concluded that the wavelength in the IR region is more safe as compared with the wavelength in the visible light regarding the light-induced damages on biological particles. This denies the possibility of using light at a wavelength in the visible light region for trapping the biological samples However, if *Escherichia coli* can be trapped alive by using a light at a wavelength in the visible light region, various advantages are obtainable compared with the use of a light in the IR light region.

In view of the above, the present inventors, et al have studied on a relationship between the wavelength of a laser light irradiated to biological particles and light-induced damages on the biological particles.

At first, according to the study of F. Bryant (Archives of Biochemistry and Biophysics, vol. 135/1969: Absolute Optical Cross Sections of Cells and Chloroplasts), it is reported that the spectral absorption of *Escherichia coli* or yeast bacteria varies in the visible light region and that this is not attributable to the light absorption of bacteria but to the scattering of light by bacteria.

When the present inventors, et al made a similar experiment for a light in a wider wavelength range of 150 to 1100 nm by a spectrophotometer using an integrating sphere, it was confirmed that the spectral absorbance changes in accordance with the wavelength as shown by a solid line in FIG. 11 and it was confirmed that *Escherichia coli* or yeast have large light absorption to the light at a wavelength of shorter than 300 nm, the light absorption is extremely small for the light in a longer wavelength region up to 1100 nm and there is a scarce difference in the absorption depending on the wavelength.

The wavelength of the light of an Ar laser (visible light: wavelength at 514 nm) at which biological damages were observed by the report of Ashkin, et al or Sakano et al is within a region of 300 to 1100 nm that does not result in light absorption upon irradiation on *Escherichia coli*, etc. and could cause no biological damages. However, since biological damages are actually observed, it is assumed that the biological damages are not caused by linear usual light absorption.

The power density of 0.64 mW/$\mu m^2$ (=640,000 kW/$m^2$) of the light used in the experiment by Sakano, et al is 640,000 times as high as the power density of 1 kW/$m^2$ of sun light irradiated on the ground in fine weather. In the field of light at such a high density, various non-linear interactions are taken place between the light and the substance irradiated therewith and two photon absorption is most likely to occur among them. The two photon absorption is the absorption caused in proportion with the square of the light intensity and does not occur at usual light intensity.

D. Dinkel, et al reported that two photon absorption was observed when a light at 580 nm was irradiated on yeast (Analytica Chemica Acta, 236/1992, Remote Two-Photon Excited Fluorescence Sensing in a Simulated Fermentation Broth). In this experiment, tryptophan as a sort of essential amino acids constituting proteins of yeast absorbed two photons at 580 nm, and took an identical excited state as if they were irradiated with UV-rays at 290 nm, i.e., one-half wavelength of 580 nm.

It can be considered that biological damages were observed for the Ar laser (visible light: wavelength at 514 nm) in the report of Ashkin, et al and Sakano, et al, not because the wavelength was in the visible light region but because the two photon absorption phenomenon resulted in the same state as that irradiated by a light at 257 nm which is one-half wavelength of 514 nm.

In view of the above, the present inventors, et al have come to a conclusion that, in a case of optically trapping biological particles such as *Escherichia coli* or yeast bacteria by a laser light, biological damages are cause in a case of using a wavelength from 150 nm to 300 nm that is absorbed by proteins or nucleic acids constituting them (FIG. 11; shown by solid line) and in a case of using a laser light having a wavelength from 300 nm and 600 nm that is absorbed by two photon absorption (FIG. 11; shown by dotted line).

Biological particles include those having dyes and not having dyes. Those not having dyes such as *Escherichia coli*, yeast bacteria and paramecium do not cause light absorption by the dyes, but those having dyes such as Euglenida, corspuscles and photosynthesis bacteria absorb light of particular colors depending on dyes thereof and, in this case, even the IR light which is considered not to cause biological damages by the existent experiment may cause biological damages.

OBJECT OF THE INVENTION

In view of the above, it is a primary object of the present invention to provide a situation in which only one micro-sample is present in a liquid medium to be sucked at once and enable to surely separate and take out only one of biological particles including those moving rapidly such as *Escherichia coli* without confirming by a microscope.

A secondary object is to enable reliable optical trapping without causing biological damages in a case of using a laser beam at a wavelength in the visible light region.

SUMMARY OF THE INVENTION

The foregoing object can be attained according to the present invention by a laser manipulation apparatus for trapping and separating an optional micro-sample from a group of micro-sample s dispersed and suspended in a liquid medium possessed in a cell plate, wherein the cell plate comprises a plate main body having a first cell for storing a liquid medium in which a great number of micro-sample s are dispersed and suspended and a second cell (11B) for storing a liquid medium in which no micro-sample s are suspended, each of the first and second cells being opened at the upper surface, spaced apart from each other by a predetermined distance, and in communication with each other by way of a narrow induction channel for inhibiting free movement of the micro-sample s, and wherein the apparatus comprises a optical trapping system for irradiating a laser light to a single micro-sample selected from the group of micro-sample s dispersed and suspended in the liquid medium stored in the first cell of the cell plate thereby trapping the single micro-sample, and a sample separation device for moving the single micro-sample from the first cell through the induction channel into the second cell by moving the cell plate or scanning the laser light in a state of trapping the single micro-sample by the optical trapping system.

According to the present invention, the liquid medium in which micro-sample s are not suspended is injected into and stored in the second cell formed to the cell plate, and then the liquid medium in which the micro-sample s are dispersed and suspended is injected into and stored in the first cell. In this case, since the first cell and the second cell are in communication with each other by way of the narrow induction channel for inhibiting the free movement of the micro-sample s, the micro-sample does not transfer to the second cell in a short period of time.

Then, the laser light is irradiated to a particular micro-sample in a plurality of micro-sample s dispersed and suspended in the liquid medium stored in the first cell to trap the particular micro-sample and then the micro-sample is moved compulsorily from the first cell through the induction channel to the second cell by moving the cell plate or scanning the laser light while trapping the micro-sample as it is.

In this case, since only one micro-sample trapped by the laser beam is moved to the second cell and only one micro-sample is present in the second cell, when the liquid medium in the second cell is sucked by a micropipette, the micro-sample is surely sucked only by one.

By closing the upper opening of the second cell with a cover sliding in the horizontal direction at the time when the liquid medium in which the micro-sample s are not suspended is injected into and stored in the second cell and then covering the upper opening of the first cell with a cover sliding in the horizontal direction at the time when the liquid medium in which micro-sample s are dispersed and suspended is injected into and stored in the first cell, since the first cell and the second cell filled with the liquid medium are tightly closed, the liquid medium is less evaporated and, accordingly, the liquid medium does not flow between each of the cells caused by evaporation.

Further, when the wavelength of the laser light irradiated for optically trapping the micro-sample is set to a visible light region of larger than 600 nm, since the wavelength is out of a range of 150 to 300 nm which is absorbed by proteins and nucleic acids constituting biological particles and is also out of a range from 300 to 600 nm which is absorbed by two photon absorption, no biological damages are caused in a case of optically trapping the biological particle not having a dye as the micro-sample.

In addition, since the light has a wavelength in a visible light region and can be recognized visually, a danger when the light enters the eye can be avoided and adjustment for the optical system when the apparatus is set is also facilitated.

Further, since the wavelength is shorter compared with the IR light, the trapping force is more intense assuming that the power of the light is identical. Further, since the beam spot diameter at the focal position is in proportion with the wavelength, the beam spot diameter is reduced as compared with the IR light and a small sample microbial can be trapped easily as compared with the IR light.

Then, if general purpose parts for usual microscopes such as lenses, mirrors and like other optical elements are used for the laser manipulation apparatus in order to reduce the cost, optical performances such as transmittance and aberration are not deteriorated thereby enabling to reduce the cost for the entire apparatus.

Further, in a case of using biological particles having a dye as the micro-sample s, if the wavelength of the laser light is selected such that it is longer than 600 nm in the visible light region and not absorbed by the dye of the micro-sample s, the wavelength is out of a range from 150 to 300 nm which is absorbed by proteins or nucleic acids constituting the biological particles, and also out of a range from 300 to 600 nm which is absorbed by two photon absorption, and the light is selected to such a wavelength as not absorbed by the dye of the micro-sample s, biological damages are not caused in a case of optically trapping the biological particle having a dye as the micro-sample.

DESCRIPTION OF THE PREFERRED EMBODIMENTS

The present invention will now be explained more specifically by way of preferred embodiments with reference to the drawings.

Figure 1:
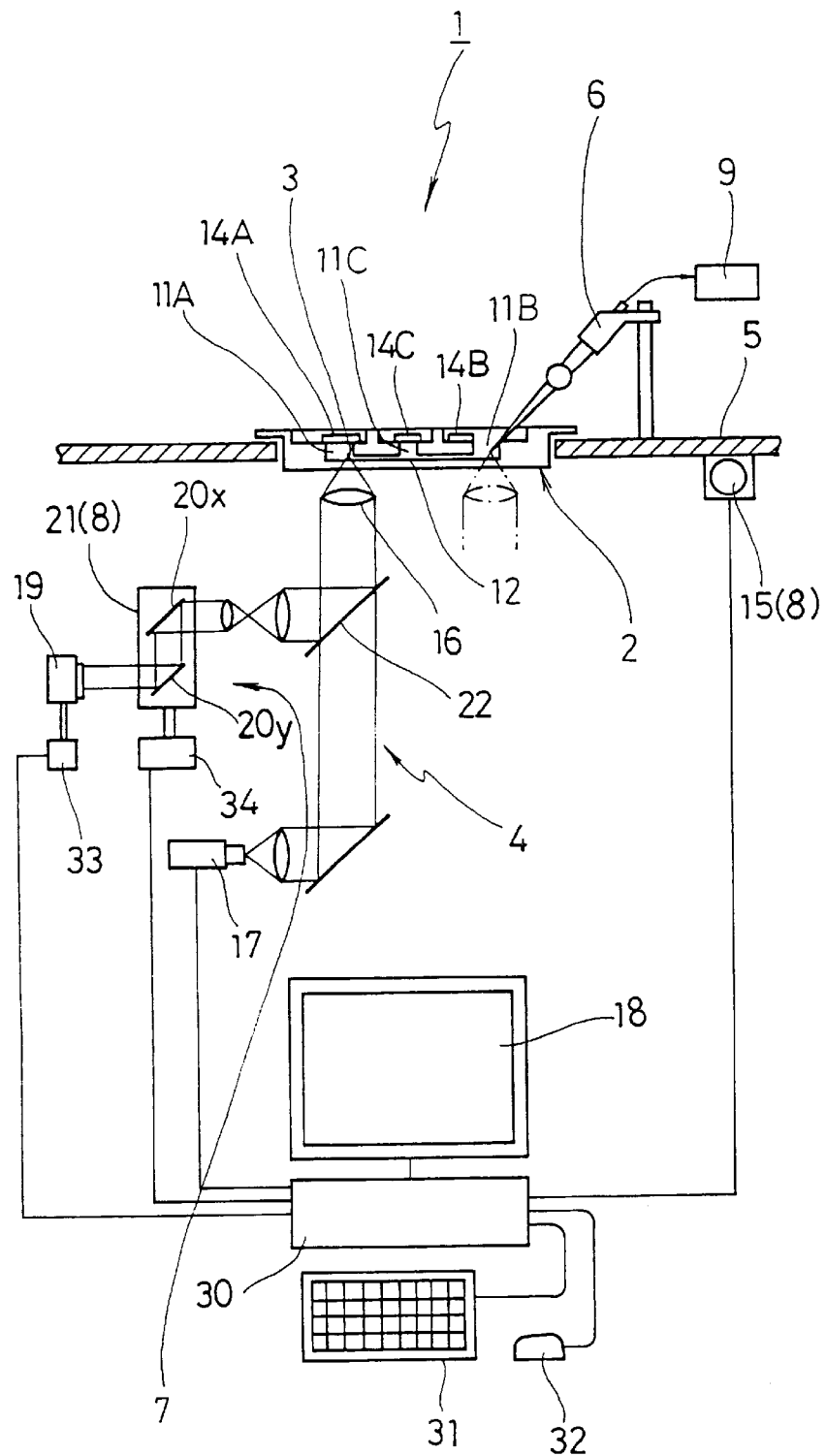
FIG. 1 is a schematic explanatory view illustrating a laser manipulation apparatus according to the present invention.
Figure 2:
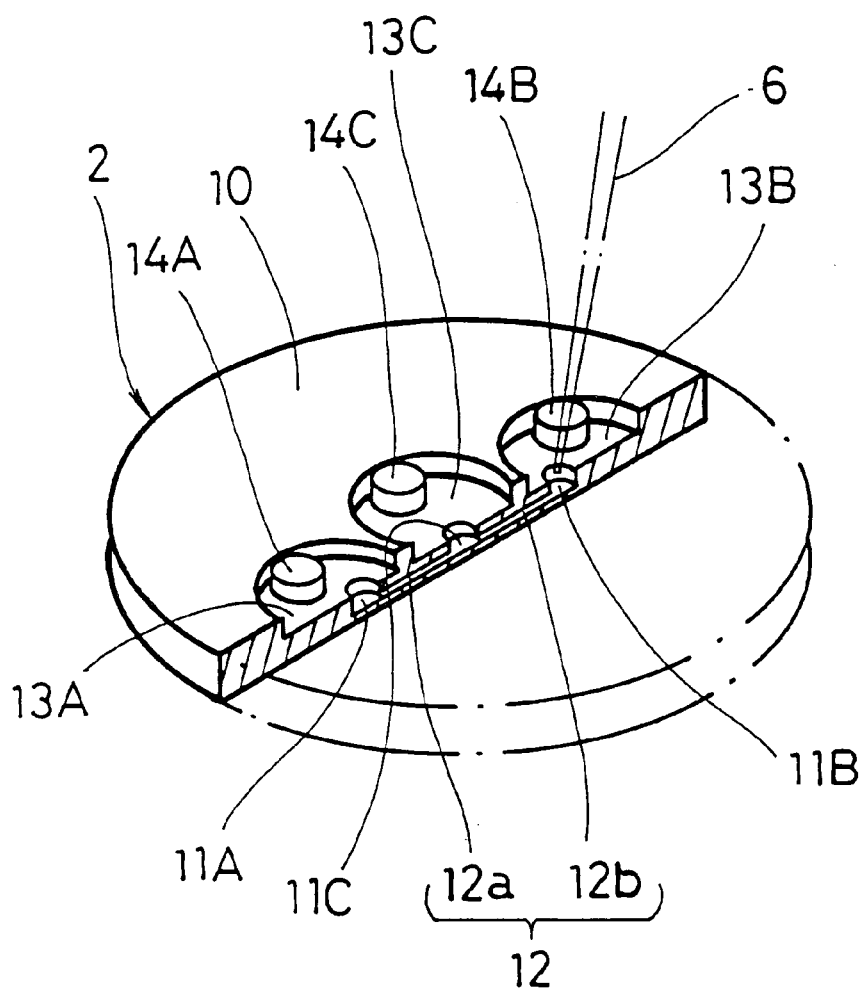
FIG. 2 is a perspective cross sectional view illustrating a cell plate used therefor.

FIG. 1 is a schematic explanatory view illustrating one embodiment of a laser manipulation apparatus according to the present invention. The laser manipulation apparatus 1 is used for taking out a single biological particle (microsample) 3 selected from a group of biological particles (group of micro-sample s) dispersed and suspended in a liquid medium possessed in a cell plate 2. The cell plate 2 is placed on a stage 5 of an inverting microscope 4, and a micropipette 6 for sucking the micro-sample 3 is disposed advanceable and retractable to the cell plate 2.

The laser manipulation apparatus 1 comprises an optical trapping system for irradiating a laser light to the micro-sample 3 selected from micro-sample s dispersed and suspended in a liquid medium under the view of the microscope 4 and trapping the micro-sample at an trapping position, a sample separation device 8 for moving the cell plate 2 or scanning laser light in a state of trapping the micro-sample 3 thereby separating the micro-sample 3 from other micro-sample s, and a sample sucking device 9 for sucking the separated particular micro-sample 3 into the micropipette 6.

The cell plate 2 for possessing the liquid medium comprises a plate main body 10 that functions as a cover glass for the inverting microscope 4, a first cell 11A for storing a liquid medium in which a great number of micro-sample s are dispersed and suspended and a second cell 11B for storing a liquid medium in which no micro-sample s are suspended. Each of the cells is opened at the upper surface and formed by being spaced apart a predetermined distance from each other and in communication with each other by a narrow induction channel 12 for inhibiting the free movement of micro-sample s.

Accordingly, the induction channel 12 has a bottom formed at a high accuracy as a cover glass for the inverting microscope 4 and has a buffer cell 11C formed with the upper surface being opened at the midway for storing a liquid medium in which no micro-sample s are suspended.

The induction channel 12 comprises a first induction channel 12a for communication between the first cell 11A and the buffer cell 11C and a second induction channel 12b for communication between the buffer cell 11C and the second cell 11B.

Each of the cells 11A–11C is formed in each of recesses 13A–13C of a larger diameter as a liquid medium injection port formed on the surface of the plate main body 10. The upper opening for each of the cells 11A–11C is adapted to be opened/closed by each of covers 14A–14C which is moved slidably in the horizontal direction along the bottom of the recesses 13A–13C.

Faces of the recesses 13A–13C and the covers 14A–14C in contact with each other are polished at a high accuracy such that they are in sliding contact at a gap formed with accuracy on the order of a wavelength of light. Then, each of the cells can be opened/closed without forming a stream in the induction channel 12 when each of the covers 14A–14C is caused to slide.

In the cell plate 2 for separating *Escherichia coli*, each of the recesses 13A–13C is about 9 mm diameter×2 mm depth, each of the cells 11A–11C is about 2 mm diameter×1.8 mm depth, the length of the induction channel 12a and 12b for communication between the cells 11A and 11C and between the cells 11C and 11B is about 9 mm, the cross section for each of the induction channel 12a, 12b is about 0.1 mm square, and the thickness for the bottom of each cell 11A–11C and the induction channel 12 is about 0.17 mm.

An objective lens 15 of the inverting microscope 4 is placed below the stage 5 disposed moveably in the direction X-Y by a stage moving device 15, a CCD camera 17 for photographing the inside of the plate 2 is set on an optical axis of the microscope, and images taken up by the CCD camera 17 are displayed on a display device 18.

The optical trapping system 7 is adapted such that the micro-sample 3 in the first cell 11A is trapped by a laser light transmitting the objective lens 16 of the inverting microscope 4. A scanning device 21 having scanning mirrors 20x, 20y for moving the trapping position of the laser light in the direction X and the direction Y and a dichroic mirror 22 are intervened in the optical channel of the laser light outputted from the laser light source 19, and the laser light reflected on the dichroic mirror 22 is adapted to transmit the objective lens 16 and converted into the first cell 11A.

In a case of optically trapping the biological sample not having a dye such as *Esecherichia coli* as the micro-sample, the wavelength of the laser light emitted from the laser light source 19 is included within a visible light region and selected to longer than 600 nm, and a semiconductor laser that oscillates a light at a wavelength of 690 nm is used in this embodiment.

As the objective lens 16, a liquid-immersed objective lens, for example, having a magnification factor of 100 and NA=1.30 is used.

The sample separation device 8 is adapted to move the micro-sample 3 from the first cell 11A through the induction channel 12 into the second cell 11B and separate the sample 3 from other micro-sample s in the first cell 11A by moving the cell plate 2 by the stage moving device 15 or scanning the laser light by the scanning device 21, in a state of trapping the particular micro-sample 3 by the optical trapping system 7.

As the sample suction device 9 for the micropipette 6, any of means can be adopted, for example, means for conducting suction/exhaustion by displacing diaphragms comprised of an elastic membrane thereby changing the volume in the pipette 6, or means for controlling the temperature in the pipette 6 and conducting suction/exhaustion by utilizing the volume change of air due to the change of temperature in the pipette. Further, the micropipette 6 is attached to the top end of a manipulator arm (not illustrated), adapted to reciprocate, for example, between the apparatus and a microplate (not illustrated) provided with culture medium, and is adapted to discharge sucked micro-sample s on a predetermined microplate.

A control device 30 for controlling the laser manipulation apparatus 1 has the CCD camera 17, a keyboard 31 and a mouse 32 connected on its input and the display device 18, the diving device 33 for the laser light source 19, the driver 34 for the laser scanning device 21 and the stage moving device 15 connected on its output.

The operation of the embodiment of the apparatus according to the present invention as described above will be explained with reference to FIGS. 3(a)–(f).

Figure 3A:
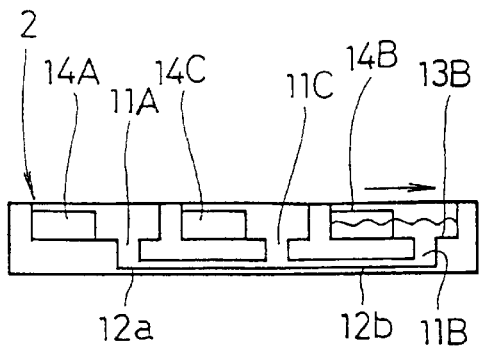
FIGS. 3(a)–(f) are explanatory views illustrating operation procedures.

At first, the cell plate 2 is set on the stage 5 and, as shown in FIG. 3(a), a clean liquid medium in which no micro-sample s are present is injected into the recess 13B in which the second cell 11B is formed and, when the cover 14B is immersed in the liquid medium, the cover 14B is caused to slide to close the upper opening of the second cell 11B. In this process, the liquid medium in the second cell 11B flows through the induction channel 12b into the buffer cell 11C by a capillary phenomenon.

Figure 3B:
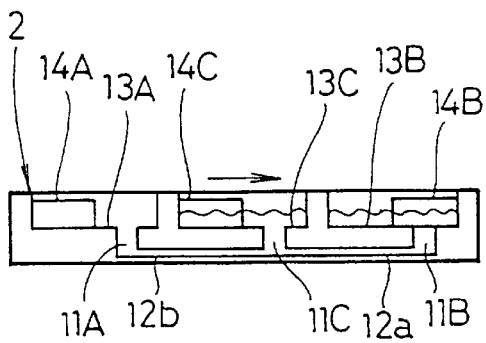

Then, as shown in FIG. 3(b), a clean liquid medium in which no micro-sample s are present is injected into the recess 13C in which the buffer cell 11C is formed and, when the cover 14C is immersed in the liquid medium, the upper opening of the buffer cell 11C is closed by sliding the cover 14C. In this step, the liquid medium in the buffer cell 11C flows in the induction channel 12a into the first cell 11A by a capillary phenomenon.

Figure 3C:
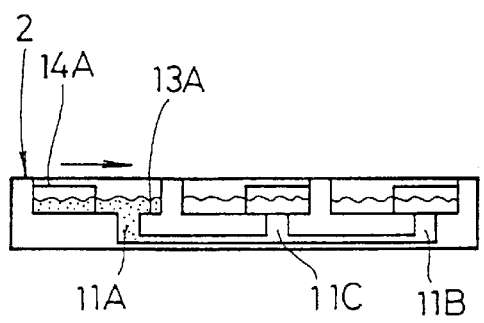

Then, as shown in FIG. 3(c), a liquid medium in which a great number of micro-sample s are dispersed and suspended is injected into the recess 13A in which the first cell 11A is formed and, when the cover 14A is immersed in the liquid medium, the upper opening of the first cell 11A is closed by sliding the cover 14A.

Since the faces of the cover 14A and recess 13A in sliding contact with each other are polished at a high accuracy, there is no worry that the liquid medium in the first cell 11A flows through the induction channels 12a, 12b into the buffer cell 11C or the second cell 11B.

Further, all of the upper openings for the cells 11A–11C are closed by the covers 14A–14C, respectively, and each of the covers 14A–14C is immersed in the liquid medium. Therefore, even when the liquid medium is evaporated, only the liquid medium stored in the recesses 13A–13C at the outside of each of the cells 11A–11C closed by the covers 14A–14C is evaporated, which gives no effect on the inside of each of the cells 11A–11C. Accordingly, the liquid medium in the cells 11A–11C is maintained in a stationary state and there is no worry of forming a stream in the induction channel 12.

Figure 3D:
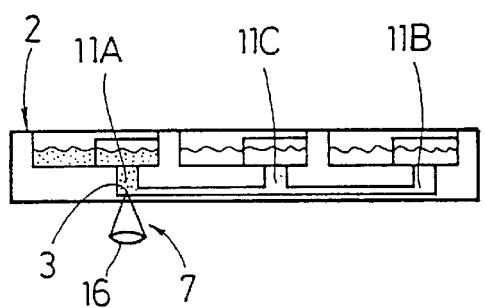

When a laser beam is irradiated by the scanning device 22 to an optional micro-sample 3 while observing the inside of the first cell 11A by the display device 14 in this state, the micro-sample 3 is trapped at that position as shown in FIG. 3(d).

Since the wavelength of the laser light is selected to 690 nm, which is out of a range for the wavelength from 150 to 600 nm at which the micro-sample 3 causes light absorption and two photon absorption, the micro-sample 3 can be optically trapped with no damages.

Figure 3E:
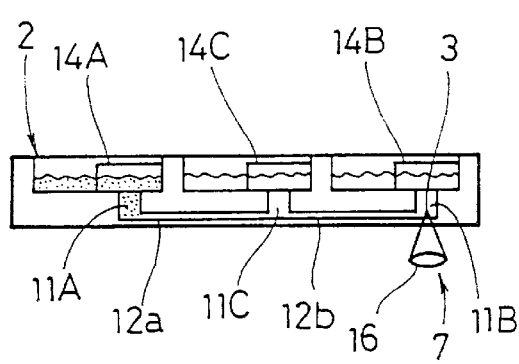

Then, as shown in FIG. 3(e), by moving the stage 5 by the stage moving device 15, the particular micro-sample 3 trapped by the laser light is moved from the first cell 11A through the induction channel 12a to the buffer cell 11C and, further, through the induction channel 12b to the second cell 11B.

In this process, since the induction channel 12 for communication between the first cell 11A and the second cell 11B is formed so narrow as capable of inhibiting the free movement of the micro-sample s, a probability that other micro-sample s in the first cell 11A swim through the induction channel 12 and reach the second cell 11B is extremely low and, accordingly, only the particular micro-sample 3 trapped by the laser beam is present in the second cell 11B.

Further, in this embodiment, since the buffer cell 11C is formed in the midway of the induction channel 12, if any micro-sample swims from the first cell 11A passing through the induction channel 12a and reaches the buffer cell 11C, it scarcely occurs that such sample from the buffer cell 11C reaches the second cell 11B passing through the induction channel 12b and, accordingly, only the particular micro-sample 3 trapped by the laser light is present and no other micro-sample s are present in the second cell 11B.

Figure 3F:
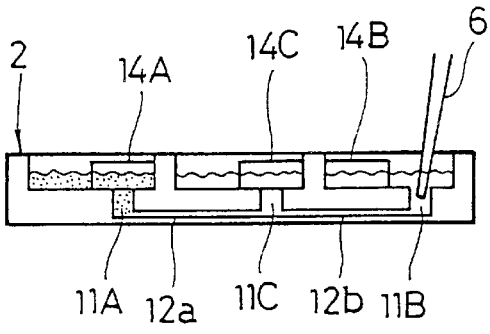

Finally, as shown in FIG. 3(f), when the upper opening of the second cell 11B is opened by sliding the cover 14B and the liquid medium in the second cell 11B is entirely sucked by the micropipette 6, only the micro-sample 3 trapped by the laser light is present in the liquid medium, a single micro-sample can surely be sucked without using no special narrow micropipette 6 or without confirming the inside of the second cell 11B by the microscope 4.

Then, the micropipette 6 is moved to the microplate provided with a culture medium (not illustrated), for example, by using a manipulator arm (not illustrated) and the micro-sample 3 is discharged together with the liquid onto in the microplate. Thus, *Escherichia coli* applied with genetic manipulation can be cultured purely from a single bacteria cell at 100% yield.

It is not limited that the buffer cell 11C is formed at the midway of the induction channel 12 only by one but may be formed by any optional number as required, and further it may be saved depending on the case.

Further, the micro-sample s are not necessarily biological particles such as *Escherichia coli* but may be other particles.

In addition, although explanation has been made in this embodiment to a case of forming the first cell 11A and the second cell 11B each by one to the cell plate, the present invention is not restricted only thereto, but the second cell 11B may be formed in plurality, each of which may be in communication the first cell 11A by way of the induction channel.

In this case, after injecting a liquid medium in which no micro-sample s are suspended in all of the second cells 11B and then closing the upper opening for each of the cells with the cover 14B, a liquid medium in which the micro-sample s are dispersed and suspended may be injected into the first cell 11A and the upper opening may be closed by the cover 14A finally.

As has been described above, in this embodiment, when the laser light is irradiated on the particular micro-sample 3, among the group of the micro-sample s dispersed and suspended in the liquid medium stored in the first cell 11A, to trap the micro-sample 3 and then the cell plate 2 is moved or the laser light is caused to scan while trapping the micro-sample 3, the micro-sample 3 can be moved from the first cell 11A through the induction channel 12 to the second cell 11B compulsorily.

As described above, when only one micro-sample trapped by the laser light is moved into the second cell 11B, since only one micro-sample is present in the second sell 11B, if the liquid medium in the second cell 11B is sucked by the micropipette, even micro-sample s swimming rapidly such as *Escherichia coli* can be surely separated and taken out only by one without confirming by the microscope, to provide an excellent effect.

According to this embodiment, since the wavelength of the laser light irradiated for optically trapping the micro-sample 3 is 690 nm, the wavelength is out of the range of 150 to 300 nm which is absorbed by proteins or nucleic acids constituting biological particle and which is also out of the range from 300 to 600 nm which is absorbed by two photon absorption, no biological damages are caused in a case of optically trapping a microbial particle not having a dye as the micro-sample.

In addition, since the wavelength is included within the region of visible light and can be observed visually, a danger upon entrance of light to an eye can be avoided, and adjustment for the optical system upon assembling the micromanipulator 1 is facilitated.

Further, since the wavelength is shorter as compared with the IR light, a trapping force is greater for the identical power of light. Further, since the beam spot diameter at the focal position is in proportion with the wavelength, the beam spot diameter is reduced as compared with that of the IR light to trap a small sample more easily compared with the IR light.

Then, even when general-purpose parts for usual microscopes at a relatively reduced cost are used as lenses, mirrors and like other optical elements for the micromanipulator 1, optical performances such as transmittance and aberration are not reduced.

In the foregoings, explanations have been made to a case of optically trapping the biological particles not having a dye such as *Escherichia coli* as the micro-sample. In a case of optically trapping a biological particle having a dye as the micro-sample, the wavelength of the laser light source 19 of the optical trapping system 7 is select ed to such a wavelength as longer than 600 nm in the visible light region and not absorbed by the dye of the micro-sample.

For example, in a case of using Euglenida as the micro-sample s, since the chlorophyll as the dye thereof absorbs light at a wavelength of from 400 to 700 nm, a laser light at a wavelength of longer than 700 nm has to be irradiated for trapping the same.

Accordingly, if the wavelength is selected so as to be out of the range of the wavelength region from 150 to 600 nm in the visible light region which is absorbed by the proteins or nucleic acids constituting the biological particles by light absorption and two photon absorption' and to a wavelength not absorbed by the dye of the biological particle, optical trapping can be carried out without causing light-induced biological damages.

In this case, if the wavelength not absorbed by the dye of the biological particle includes the wavelength of the visible light region, the foregoing advantages can also be obtained by using the light of such a wavelength as described above compared with the case of using the IR light.

If the wavelength of the laser light for conducting optical trapping is selected to longer than 600 nm in the visible light region, since this is out of the range of the wavelength from 150 to 600 nm of the light that causes light absorption and two photon absorption in the biological particle, biological damages are not caused in a case of optically trapping the biological particle riot having a dye as the micro-sample.

Further, since the wavelength is included in the region of the visible light and can be observed visually, a danger, if the light enters an eye, can be avoided, as well as adjustment for the optical system when the apparatus is set is also facilitated.

Further, since the wavelength is shorter as compared with the IR light, the trapping force is more intense for the identical power of light and since the beam spot diameter at the focal point is smaller as compared with that of the IR light, a small sample can be trapped easily compared with the IR light.

Furthermore, it also provides an excellent effect that optical performances such as transmittance and aberration are not reduced even when general-purpose parts for usual microscopes are used as lenses, mirrors and like other optical elements for the laser manipulation apparatus, whereby the entire cost of the apparatus can be reduced.

Further, in a case of using biological particles having a dye as the micro-sample s, if the wavelength of the laser light is set to such a wavelength as longer than 600 nm in the visible light region and not absorbed by the dye of the micro-sample s, it can provide an advantageous effect capable of surely trapping, without causing biological damages, even those biological particles suffering from biological damages when trapped optically by the IR light which has been considered not to cause biological damages.

Figure 4:
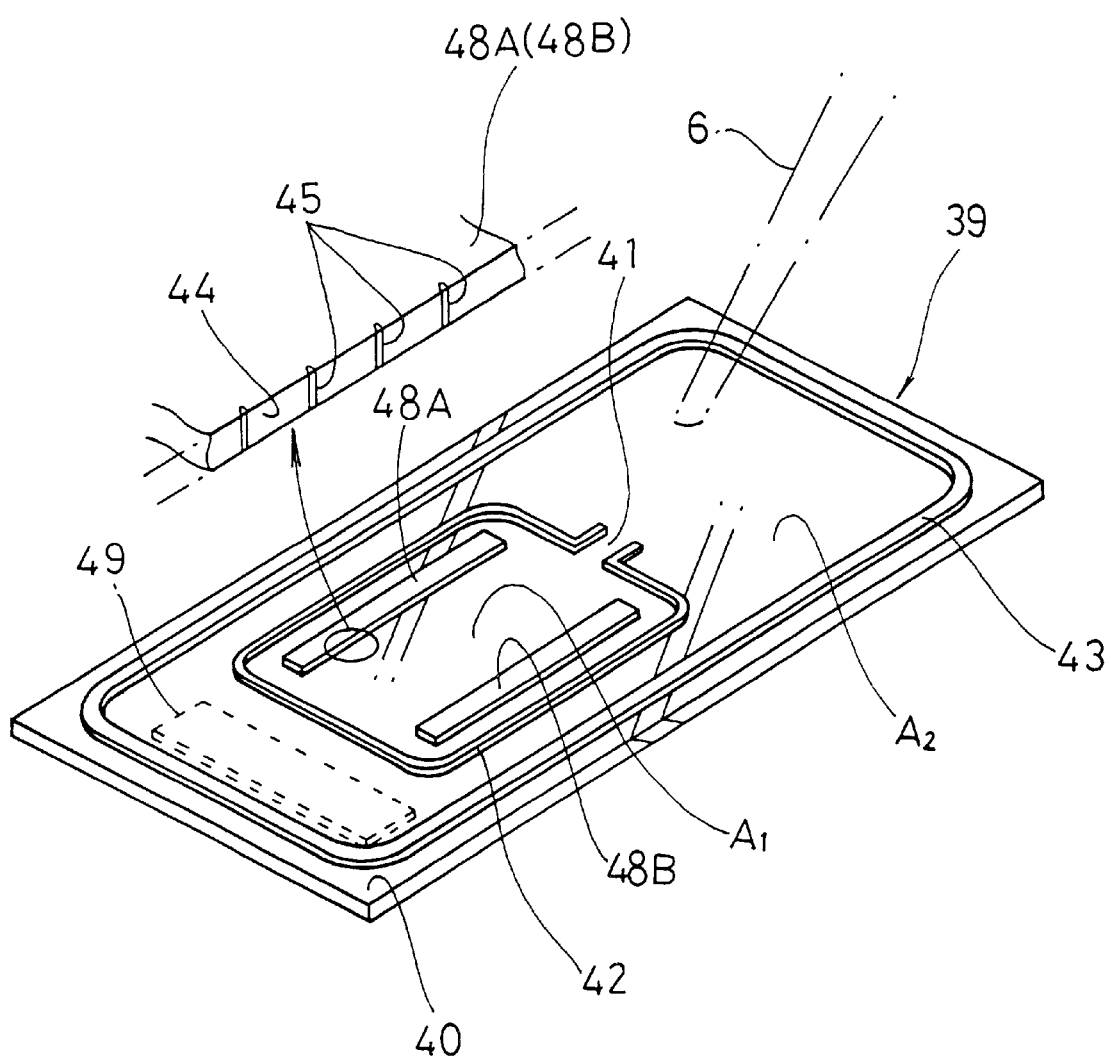
FIG. 4 is a perspective view illustrating another cell plate.
Figure 5:
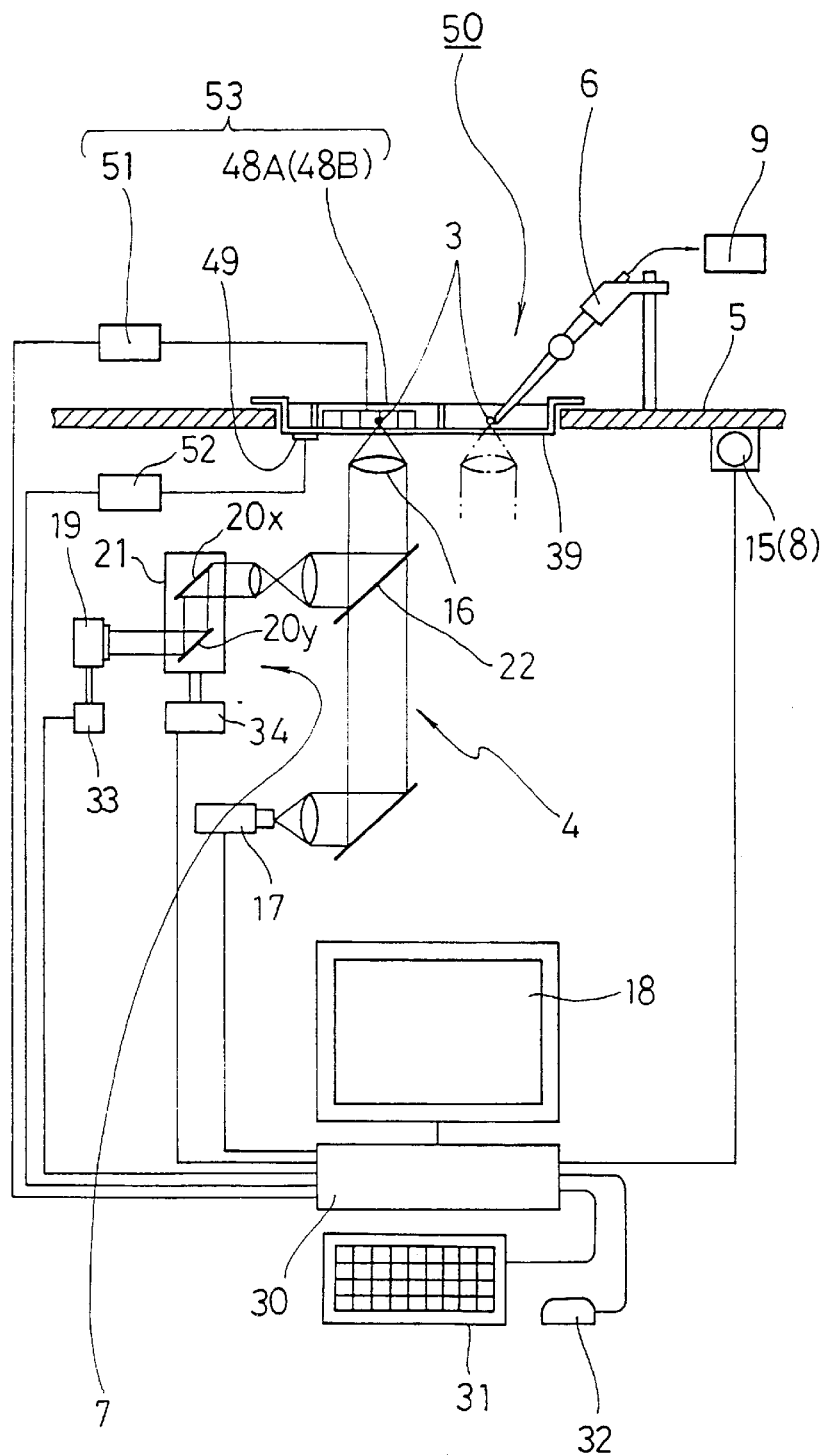
FIG. 5 is a schematic explanatory view illustrating another laser manipulation apparatus.

FIG. 4 is a perspective view illustrating another cell plate 39, for example, with an extremely thin glass plate. On the plate surface 40, are formed a first region $A_1$ for trapping a particular micro-sample 3 in a liquid medium by the irradiation of a laser light and a second region $A_2$ for sucking the micro-sample 3 trapped by the laser light with a micropipette 6, the first and the second regions being communicated with each other by way of a channel 41.

A partition wall 42 for partitioning each of the regions $A_1$ and $A_2$ and a surrounding wall 43 for surrounding the plate surface 40 are formed, for example, by depositing a resin on the plate surface 40 by a photoresist or printing method.

Each of the regions $A_1$ and $A_2$ may be formed by disposing a recess in the plate surface 40.

Electrodes 48A and 48B are disposed in the first region $A_1$ for forming a not-uniform electric field in the liquid medium.

Figure 6:
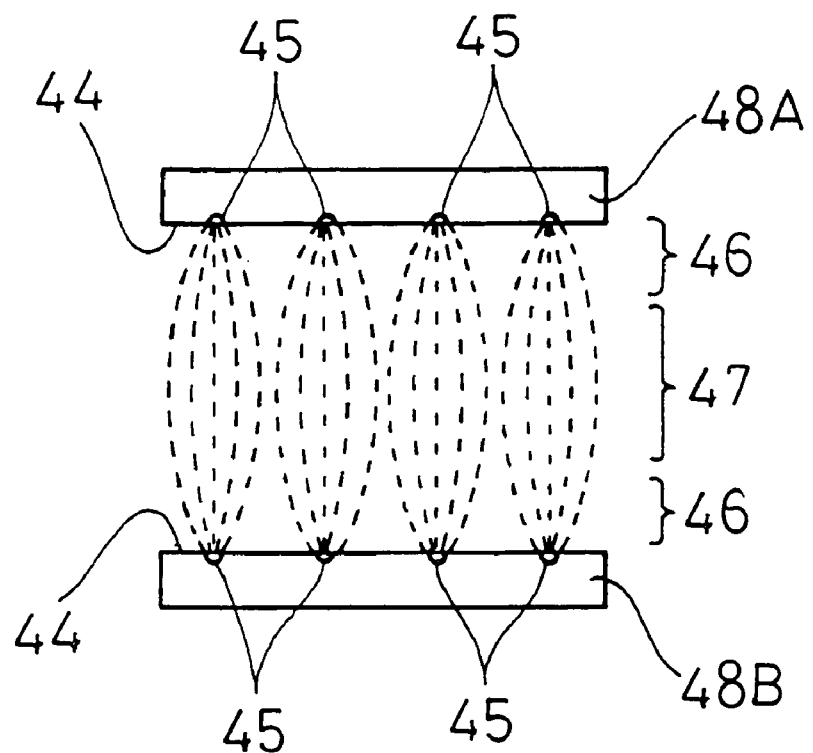
FIG. 6 is a conceptional view for a not uniform electric field formed between electrodes.

In the electrodes 48A, 48B, a plurality of linear conductors 45, 45, - - - are buried each at a predetermined distance on the faces 44 opposite to each other, and a not uniform electric field as shown in FIG. 6 is formed by applying AC or DC voltage between each of the electrodes 48A and 48B.

In this electric field, since lines of electric force are radially diverged from each of the linear conductors 45 on one electrode 48A and converged into each of the linear conductors 45 of another electrode 48B, the density of the lines of electric force is high and, accordingly, the electric field is intense in the vicinity 46 for the electrodes 48A, 48B, whereas the density of the lines of electric force is low and, accordingly, the electric field is weak at the intermediate portion 47 between the electrodes 48A and 48B, so that a not uniform electric field is formed as a whole.

The shape of the electrodes 48A and 48B is not restricted only to the illustrated embodiment but, for example, one of them may be a spot or linear electrode, while the other of them may be a planer shape. In summary, it may be any of shapes providing that the density of the lines of electric force changes in accordance with the distance to the electrode.

Further, an oscillator 49 such as piezoelectric ceramic material, piezoelectric element or super magnetostrictive element is attached to the rear face of the cell plate 39, so that biological particles or micro particles deposited on the plate surface 40 are shaken off by applying supersonic vibrations to the cell plate 39.

Since the laser manipulation apparatus 50 is identical with the laser manipulation apparatus 1 shown in FIG. 1 excepting that a radiowave oscillator 51 forming an AC electric field at a high frequency of about 1 MHz between the electrodes 48A and 48B, and a vibration generation device 52 for driving the oscillator 49 are connected to a control device 30 those portions in common with them carry the same reference numerals, for which detailed explanations are to be omitted.

The electrodes 48A, 48B and the radiowave oscillator 51 constitute an electric adsorption device 53 for adsorbing the group of micro-sample s dispersed and suspended in the liquid medium of a first region $A_1$ to the electrodes 48A and 48B.

The constitution for the embodiment of the apparatus is as has been described above and now the operation will be explained with reference to FIGS. 7(a)–(d).

At first, the cell plate 39 is set on the stage 5 and a liquid medium containing a great number of biological particles (for example, *Escherichia coli*) is dropped in a first region $A_1$, and a liquid medium not containing biological particles is dropped into the second region $A_2$ as shown in FIG. 7(a).

Since the biological particles in the first region $A_1$ swim from the channel 41 into the second region $A_2$ if they are left as they are, an AC current is instantly applied from the radiowave oscillator 51 to the electrodes 48A, 48B to form a not uniform electric field. Then, the biological particles cause dielectrophoresis and move toward each of the electrodes 48A, 48B.

That is, electrically neutral biological particles or like other particles present in the electric field cause polarization and positive and negative charges are induced on both ends equally in an amount. Since the not uniform electric field is formed in the liquid medium, balance of the electric force is lost to bring about dielectrophoresis phenomenon in which the biological particles or like other particles are moved phoretically toward the higher electric field density.

Figure 7:
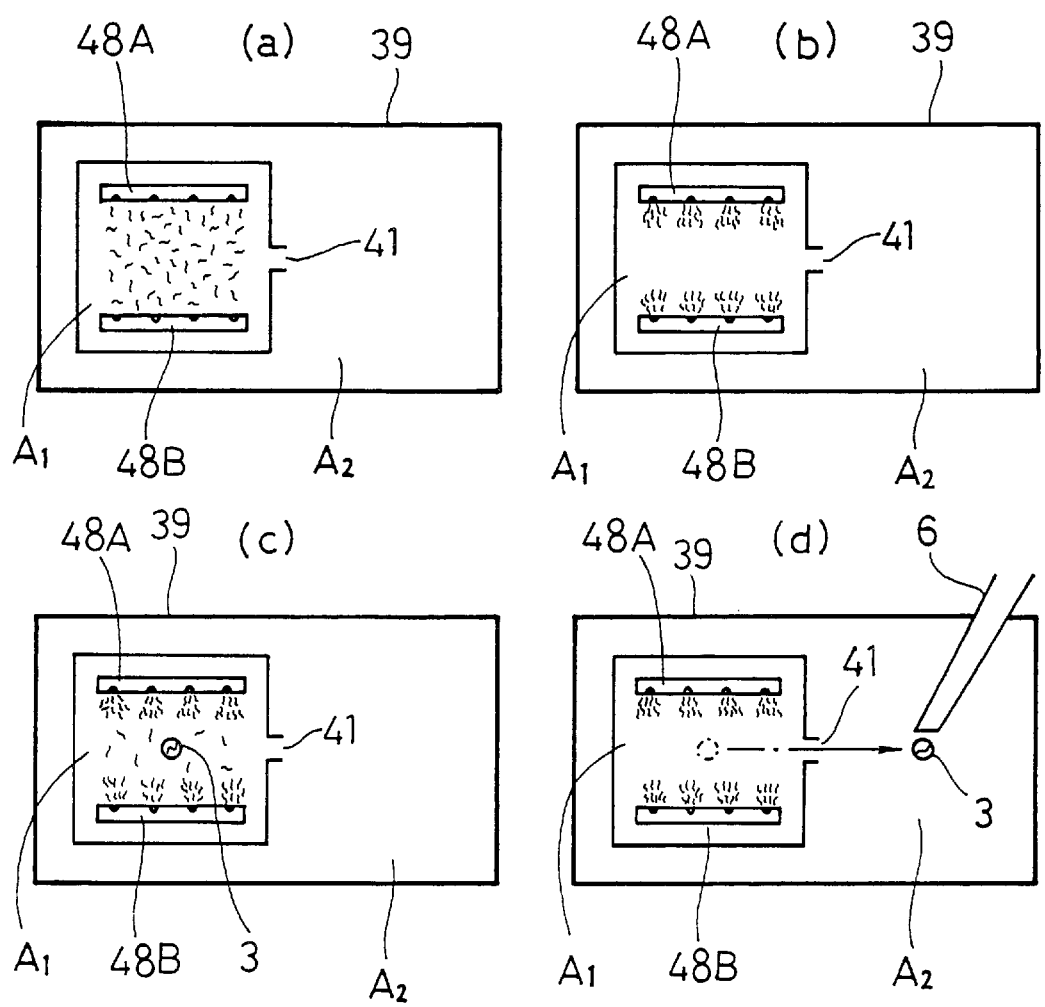
FIGS. 7(a)–(d) are explanatory views illustrating operation procedures.

In this way, the biological particles are adsorbed to each of the electrodes 48A, 48B and confined within the first region $A_1$ as shown in FIG. 7 (b).

In this case, an AC voltage at about 400 V/cm and 1 MHz is applied between the electrodes 48A and 48B when the liquid medium has resistivity, for example, of 10 KΩ·cm or greater.

Then, when the voltage applied between the electrodes 48A and 48B is momentarily interrupted, the not uniform electric field disappears and, as shown in FIG. 7(c), the biological particles adsorbed on the electrodes 48A, 48B leave the electrodes and start to swim. Then, when a laser light is irradiated from the scanning device 21 to a particular micro-sample 3 at an intermediate position between the electrodes 48A and 48B while observing them on the display device 18, the micro-sample 3 is trapped at that position.

Then, when the AC voltage is applied again between the electrodes 48A and 48B, since the not-uniform electric field is formed, as shown in FIG. 7(d), the group of micro-sample s other than the particular micro-sample 3 trapped by the laser beam are adsorbed again on the electrodes 48A and 48B and the micro-sample 3 is separated from the group of other micro-sample s.

Then, by driving the scanning device 21 to scan the laser light or by moving the stage 5 by the stage driving device 15, the particular micro-sample 3 trapped by the laser beam is moved from the first region $A_1$ through the channel 41 into the second region $A_2$ and positioned at the top end (sucking position) of the micropipeztte 6 previously protruded into the liquid medium.

Then, when the micro-sample 3 is sucked into the micropipette 6 by operating the suction device 9 while lowering the output of the laser light to such an extent that the micro-sample 3 is not moved out of the laser spot, the micro-sample can be trapped surely only by one without moving the micropipette 6.

Further, since other micro-sample s are adsorbed on the electrodes 48A, 48B, they do not swim into the second region $A_2$ and only the particular micro-sample 3 trapped by the laser beam is present in the second region $A_2$, only one particle can be surely sucked into the micropipette even if the diameter at the top end of the micropipette 6 is somewhat large.

Then, the micropipette 6 is moved to a microplate provided with culture medium (not illustrated), for example, by a manipulator arm (not illustrated) to discharge the micro-sample 3 onto the micro plate.

Thus, *Escherichia coli* applied with genetic manipulation can be cultured purely at 100% yield from one cell for instance.

Figure 8B:
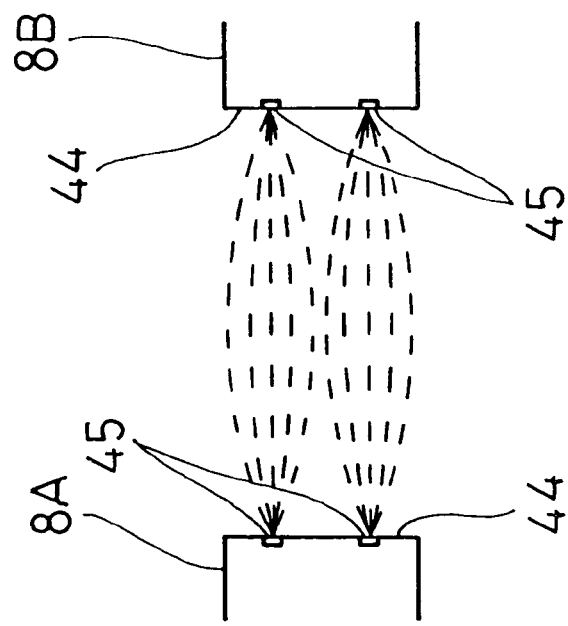
FIG. 8(a), (b) are, respectively, a perspective view and an electric field conceptional view illustrating another electrodes.
Figure 8A:
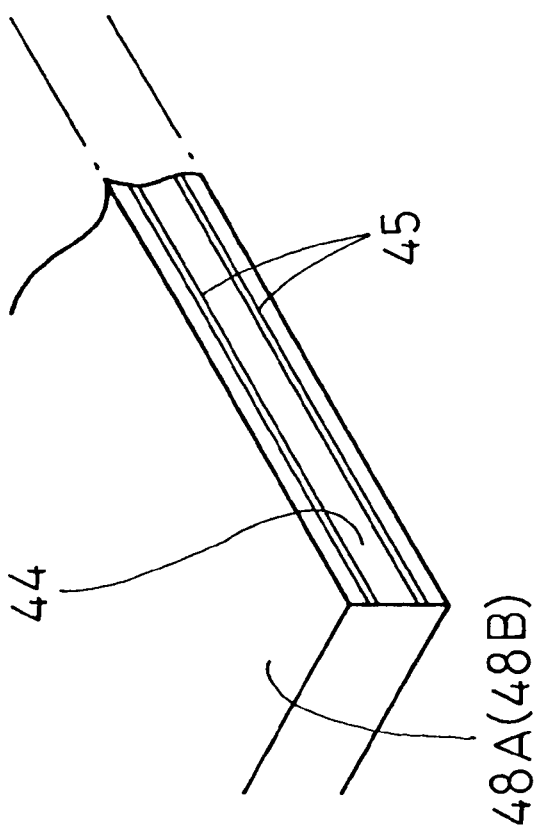

The electrodes 48A and 48B are not restricted only to the constitution shown in FIG. 4 but they may be constituted by disposing linear conductors 45 along a Longitudinal direction to surfaces 44 opposed to each other as shown in FIG. 8(a). In this case, an electric field not uniform in the direction of the thickness is formed as shown in FIG. 8(b).

In a case of adsorbing charged particles, etc. by electrophoresis, since it may suffice to form an electric field regardless that the electric field is uniform or not, the electrodes 48A, 48B may be formed with plate-like conductors and surfaces of them may be opposed to each other.

Figure 9:
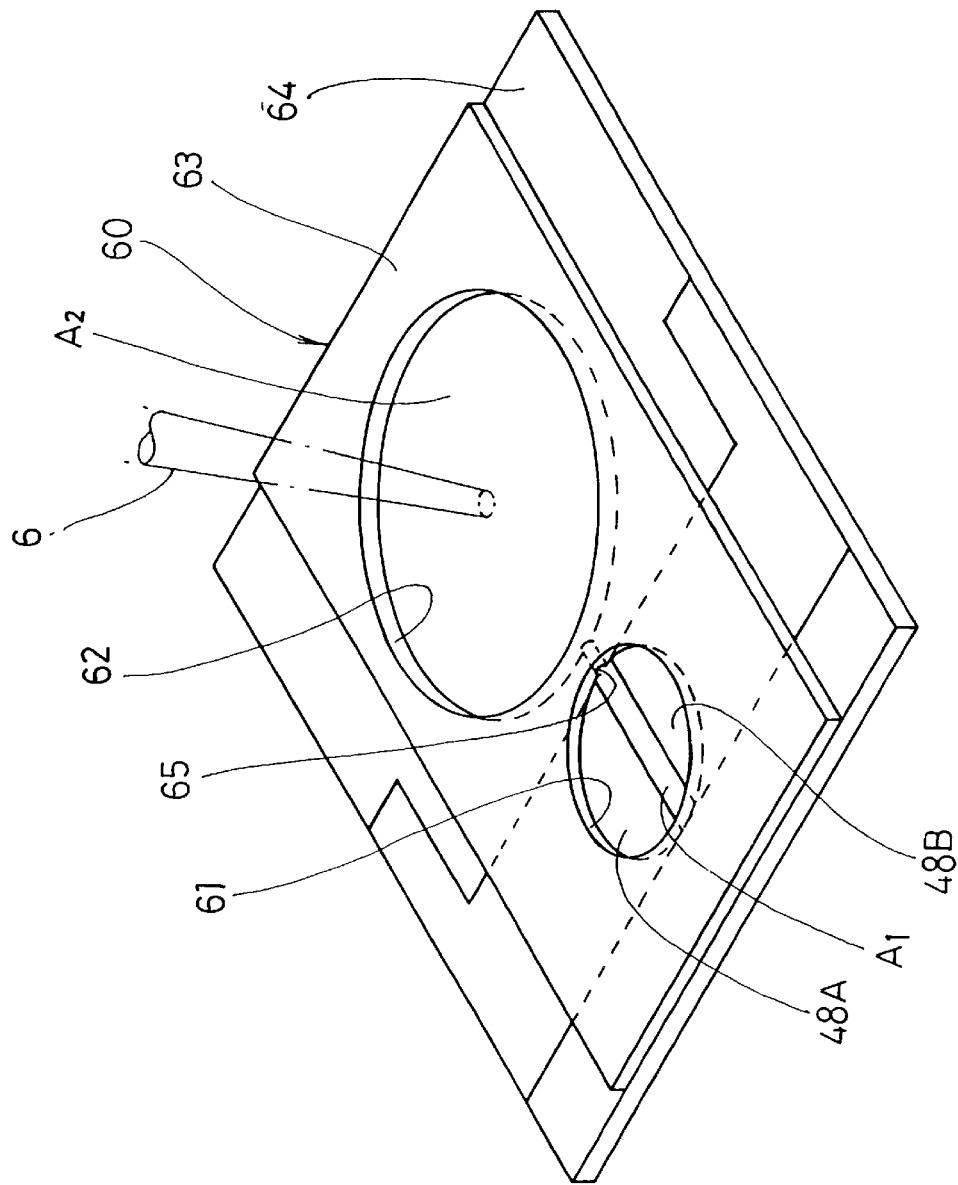
FIG. 9 is a perspective view illustrating a further embodiment of the cell plate.

FIG. 9 is a perspective view illustrating a further cell plate 60. In this embodiment, a cover plate 63 having two circular holes 61 and 62 formed therein is stacked on a substrate 64. A recess defined with the circular hole 61 and the substrate 64 constitute a first region $A_1$ for trapping a particular micro-sample 3 or like other particle in a medium by irradiation of a laser light, and a recess defined with the circular hole 62 and the substrate 64 constitute a second region $A_2$ for sucking a particular micro-sample 3 or like other particle trapped by the laser light by a micropipette.

A groove constituting a tunnel type channel 65 is formed at the bottom of the cover plate 63 for communication between each of the regions $A_1$ and $A_2$ when the cover plate 63 and the substrate 64 are stacked.

Thin film electrodes 48A, 48B formed by vapor deposition of aluminum is disposed on the substrate at a position where the circular hole 61 as the first region $A_1$ is stacked.

In this embodiment, a medium as a specimen in which micro-sample s are present in admixture is filled in the first region $A_1$ and a medium not containing the micro-sample s is filled in the second region $A_2$, a laser light is irradiated to trap an optional micro-sample 3, an electric field is formed between the electrodes 48A and 48B to adsorb other micro-sample s on the electrode 48A, 48B and then the particular sample 3 is transferred through the tunnel type channel 65 into the second region $A_2$.

Then, when the micro-sample 3 transferred to the second region $A_2$ is sucked by a micropipette 6, since only the particular micro-sample 3 trapped by the laser beam is present in the second region $A_2$, only one sample can surely be sucked into the micropipette 6 even if the diameter for the top end of the micropipette 6 is somewhat large.

Figure 10:
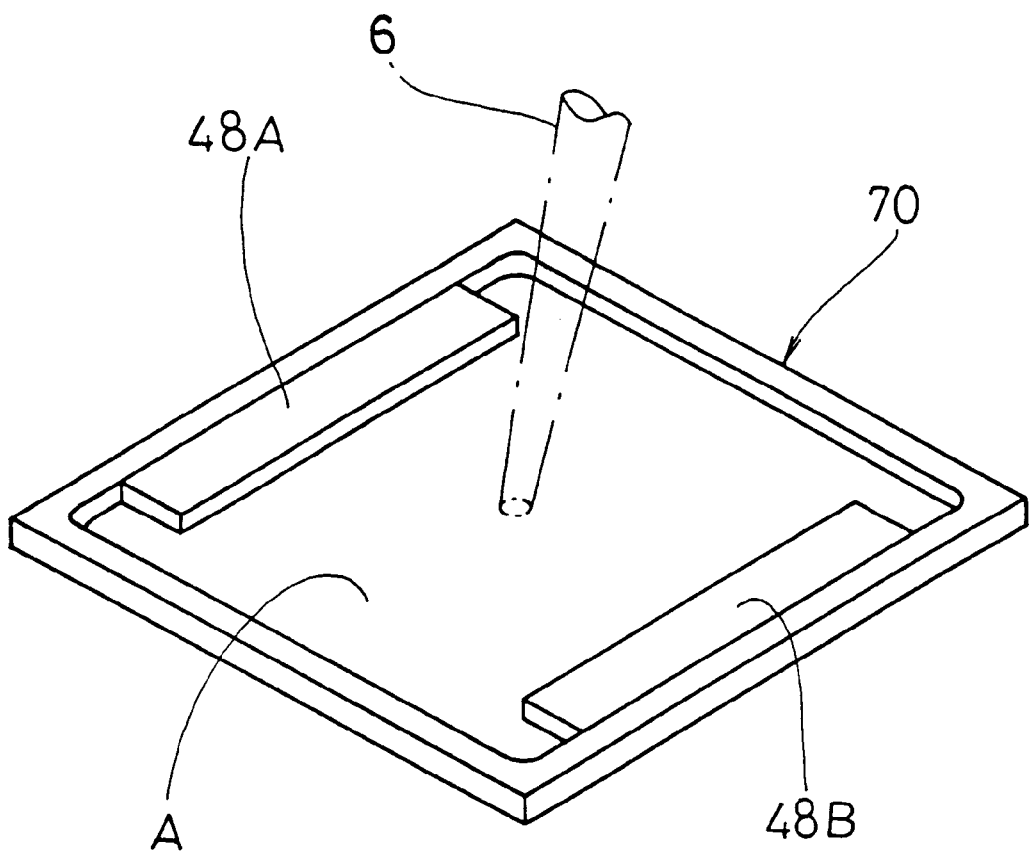
FIG. 10 is a perspective view illustrating a still further embodiment of the cell plate.
Figure 11:
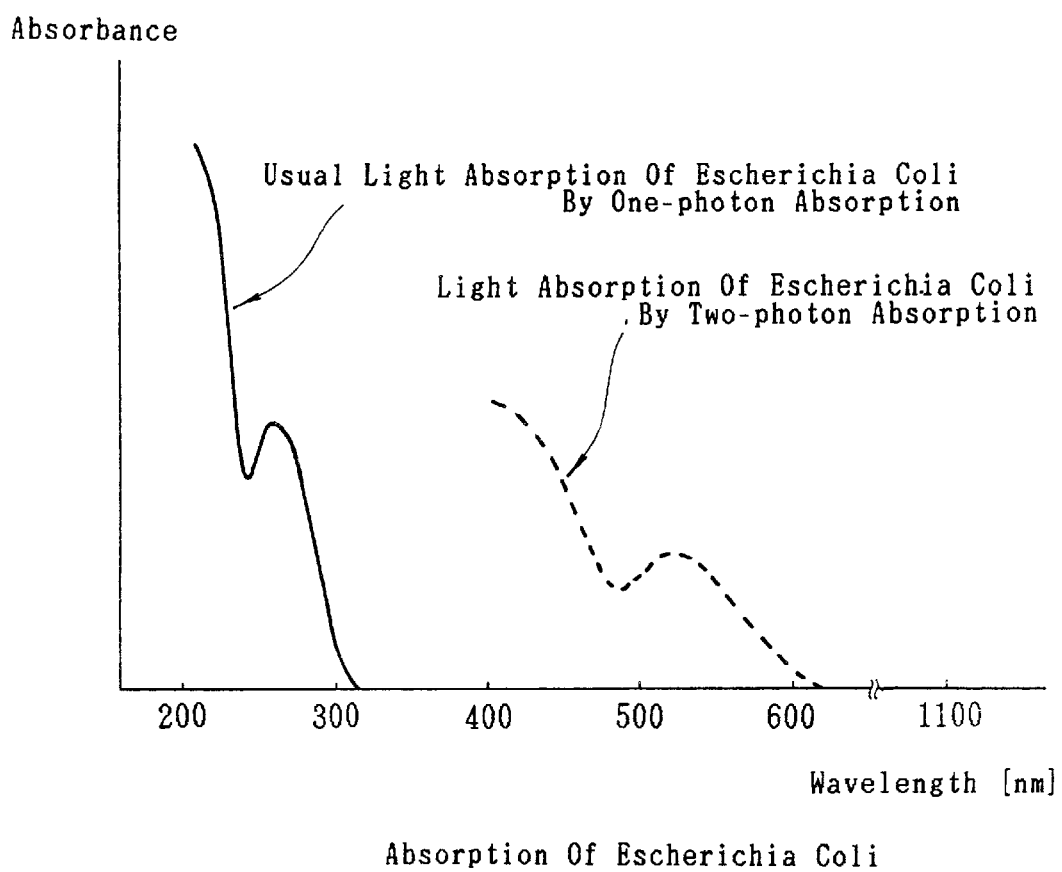
FIG. 11 is a graph illustrating absorption of *Escherichia coli*.

FIG. 10 is a perspective view illustrating a still further cell plate 70. In this embodiment, a region A is formed for sucking the particular micro-sample 3 or like other particle into a micropipette 6 in a state while trapping the sample in the medium by the irradiation of a laser light, and at least a pair of electrodes 48A and 48B for forming the electric field in the medium are formed with the region A being put between them.

In this embodiment, the medium as the specimen in which micro-sample s are present in admixture is filled in the region A, and the laser light is irradiated in the region A to trap an aimed micro-sample 3, while an electric field is formed between the electrodes 48A and 48B to adsorb other micro-sample s to the electrodes 48A and 48A.

Then, when the micropipette 6 is advanced to the irradiation position of the laser light in this state to suck the trapped micro-sample 3, since only the particular micro-sample trapped by the laser beam is present in the vicinity thereof, only one sample can surely be sucked into the micropipette 6 even if the diameter at the top end of the micropipette 6 is somewhat large.

As has been described above, it is possible to trap and stop the movement of a particular biological particle or like other particle among the group of micro-sample s or the group of other particles by the optical trapping system, and adsorb the group of biological particles or the group of micro samples other than the trapped particular biological particle or like other particle on the electrodes by the electric adsorption means utilizing the dielectrophoresis and electrophoresis.

When the particular microbiological sample or other particle trapped by the laser light is sucked by the micropipette in the state, since only one biological particles or other particles is positioned near the top end of the micropipette and no other biological particles or other particles are present, this provides an excellent effect capable of surely sucking only one micro-sample or other particle even if the micropipette of a relatively large top end is used.

What is claimed is:

1. A laser manipulation apparatus for irradiating a laser light through a converging optical system (16) having a focal point in a medium in which micro-sample s are suspended to said medium, and concentrating the laser light to the focal position of the converging optical system (16) thereby optically trapping a micro-sample (3) at the focal position, wherein the wavelength of the laser light is selected such that it is included within a region of visible light and longer than 600 nm, in a case of optically trapping biological particles not having a dye as micro-sample s.

2. A laser manipulation apparatus for irradiating a laser light through a converging optical system (16) having a focal point in a medium in which a micro-sample s are suspended to said medium, and concentrating the laser light to the focal position of the converging optical system (16) thereby optically trapping a micro-sample (3) at the focal position, wherein the wavelength of the laser light is selected such that it is longer than 600 nm in the visible light region and not absorbed by a dye of the micro-sampler s in a case of optically trapping biological particles having a dye as the micro-sample s.

* * * * *